US00PP26447P2

(12) United States Plant Patent
Hansen

(10) Patent No.: US PP26,447 P2
(45) Date of Patent: Mar. 1, 2016

(54) ***MONARDA* PLANT NAMED 'LEADING LADY PLUM'**

(50) Latin Name: ***Monarda didyma*×*Monarda bradburiana***
Varietal Denomination: Leading Lady Plum

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 109 days.

(21) Appl. No.: 14/120,592

(22) Filed: Jun. 6, 2014

(51) Int. Cl.
*A01H 5/02* (2006.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct cultivar of ornamental cultivar of ornamental bee balm plant named *Monarda* 'Leading Lady Plum' has short, compact, winter-hardy, clumping habit, dark green, and powdery mildew tolerant foliage. The magenta-purple flowers are at least two weeks earlier than *Monarda didyma* cultivars accented by rows of darker reddish-purple spots and continue for 5 to 8 weeks with branched stems developing above the terminal flower branches. The verticillasters are accented by greyed-purple bracts and sepals.

1 Drawing Sheet

BOTANICAL DESIGNATION AND CULTIVAR DENOMINATION

Botanical classification: *Monarda didyma*×*Monarda bradburiana*.

Variety denomination: 'Leading Lady Plum'.

FEDERAL SPONSORSHIP AND FUNDING

This plant invention was developed without federally sponsored research or development funding.

BACKGROUND OF THE INVENTION

The present invention relates to the new and distinct cultivar of Bee balm, botanically known as *Monarda* 'Leading Lady Plum', and hereinafter also referred to solely as the cultivar 'Leading Lady Plum' or the "new plant." *Monarda* 'Leading Lady Plum' was hybridized in the summer of 2009 at a wholesale perennial nursery in Zeeland, Mich., USA by the inventor and given the original breeder code of H9-38-02. The new plant was separated out for further evaluation in the summer of 2010 in the full sun trial gardens of the same nursery in Zeeland, Mich., as a planned breeding program to produce new colored Bee balm flowers with superior mildew resistance, new and improved flowers and compact habit. The new plant has been asexually propagated since 2011 by stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Leading Lady Plum' is unique from its parents and all other bee balm plants known to the inventor. The nearest comparison varieties are a sibling, *Monarda* 'Leading Lady Lilac' (co-pending U.S. Plant patent application Ser.

No. 14/120,589) and the two parents, *Monarda* 'Coral Reef' U.S. Plant Pat. No. 16,741, and a proprietary selection of *Monarda bradburiana* (not patented). *Monarda* 'Coral Reef' is much taller and has a more pinkish-colored flower without spotting than the shorter habit and darker magenta-purple colored and spotted flower of the new plant. The selection of *Monarda bradburiana* has similar darker reddish-purple accent spots in the flower like that of *Monarda* 'Leading Lady Plum', but it is lighter in the background petal and is more spreading and taller in habit than the new plant. The habit and spotted petals of 'Leading Lady Plum' is most similar to its sister sibling 'Leading Lady Lilac' except the flower color of 'Leading Lady Plum' is more magenta-purple based and the flower color of 'Leading Lady Lilac' is more light lilac. Both *Monarda* 'Leading Lady Plum' and *Monarda* 'Leading Lady Lilac' flower about two weeks earlier in trials in Michigan and North Carolina than all other *Monarda didyma* cultivars tested and have flowering side branches that develop above the terminal branch effectively extending the fresh flowering appearance of the new plant.

The new plant *Monarda* 'Leading Lady Lilac' is distinct from all bee balm plants known to the inventor. Table 1 compares two main traits of several of the nearest comparison cultivars with corresponding U.S. Plant Patent numbers listed where relevant.

TABLE 1

| CULTIVAR | HEIGHT | FLOWER COLOR |
|---|---|---|
| 'Achall' PP19582 | 45 cm | deep red-purple |
| 'Acrade' PP19580 | 40 cm | purple violet |
| *M. bradburiana* | 45 cm | light lavender with dark spots |
| 'Coral Reef' PP16741 | 125 cm | coral pink |
| 'Fire Marshall' PP23286 | 50 cm | deep red |
| 'Fireball' PP14235 | 60 cm | red-purple |
| 'Leading Lady Lilac' | 32 cm | light lilac purple with dark spots |

TABLE 1-continued

| CULTIVAR | HEIGHT | FLOWER COLOR |
|---|---|---|
| 'Leading Lady Plum' | 34 cm | magenta purple with dark spots |
| 'MCmum' PP22136 | 60 cm | pink |
| 'Mondid 0803' PP17513 | 40 cm | red-purple |
| 'Pardon My Pink' PP24244 | 28 cm | fuchsia-pink |
| 'Pardon My Purple' PP22170 | 30 cm | dark fuchsia |
| 'Petite Delight' PP10784 | 30 cm | light pink-purple |
| 'Petite Wonder' PP13149 | 25 cm | light pink |
| 'Pink Lace' PP18367 | 45 cm | red-purple |
| 'Pink Supreme' PP14204 | 60 cm | dark pink |
| 'Sugar Lace' PP22918 | 44.5 cm | red-purple |

The following are traits of *Monarda* 'Leading Lady Plum' that in combination distinguish it from all other bee balm known to the inventor:

1. Short, compact, winter-hardy, clumping habit.
2. Dark-green, slightly-glossy, powdery mildew tolerant foliage.
3. Compact magenta-purple flowers for a long period beginning late spring at least two weeks earlier than most *Monarda didyma* cultivars.
4. Inside lower flower petals accented by rows of darker reddish-purple spots.
5. Flowers in dense verticillasters subtended by bracts of blackish-purple tinting.
6. Lateral flowering branches extend above terminal flowers extending the fresh appearance.

BRIEF DESCRIPTION OF THE DRAWINGS

The photographs of the new plant demonstrate the unique traits of *Monarda* 'Leading Lady Plum' and the overall appearance of the plant at two-years old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
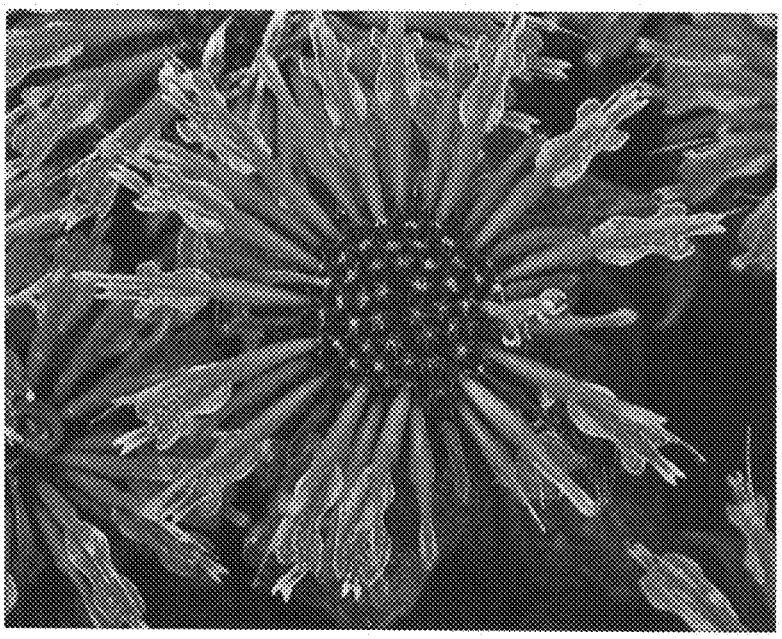
FIG. 1 shows a close-up of the flower of the new plant.
Figure 2:
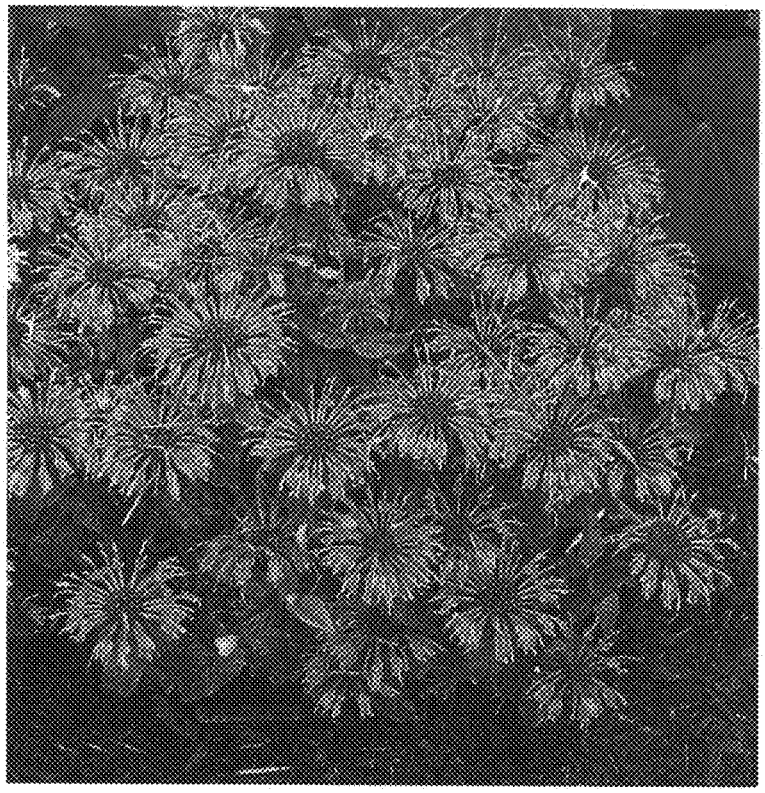
FIG. 2 shows the habit of the new plant in flower.

The following descriptions and color references are based on The 2001 Edition of The Royal Horticultural Society Colour Chart except where common dictionary terms are used. *Monarda* 'Leading Lady Plum' has not been observed under all possible environments. The phenotype may vary slightly with different growing environments such as temperature, light, fertility, soil pH, moisture and maturity levels, but without any change in the genotype. The following observations and size descriptions are based on two-year old full-sun, trial garden-grown plants at a nursery in Zeeland, Mich. with limited supplemental fertilizer and water as needed but without plant growth regulators or pinching. Where significant differences occur characteristics compared with two-year old greenhouse forced plants with supplemental lighting, fertilizer and water.

Botanical classification: *Monarda didyma*×*Monarda bradburiana.*

Parentage: Female (seed) parent is *Monarda didyma* 'Coral Reef' U.S. Plant Pat. No. 16,741; male (pollen) parent is a proprietary selection of *Monarda bradburiana* (not patented).

Plant habit: Hardy herbaceous perennial, compact, producing several stems spreading by short rhizomes near the base of the stems; 28 to 34 cm tall at flowering and 56 to 66 cm wide; flowering begins late spring in Michigan and continuing for about 5 to 9 weeks.

Propagation: Stem cuttings.

Time to produce finished crop in 3.8 liter pots: About 7 to 9 weeks; moderate rate of growth.

Root: Fine, fibrous and freely branching; color creamy white to tan depending on soil type.

Foliage fragrance: Pleasantly lemony.

Leaves: Simple, lanceolate, opposite, serrated, puberulent above and below; lustrous above, semi-lustrous to matte below; acute apex, ovate to rounded base; about 5.5 to 9.0 cm long by 3.5 to 5.5 cm wide, average about 7.2 cm long and 4.0 cm wide.

Leaf color: Young leaves between RHS 144B and N144C above, nearest RHS 144C below with tinting mostly around margin above and below of nearest RHS N186B; older leaves between RHS 139A and RHS 136A above and between RHS 146A and RHS 137B below; greenhouse forced foliage of older leaves nearest RHS 136A above and between RHS 138A and RHS 138B below; with tinting above and below of nearest RHS N186B.

Veins: Pinnate; pubescent below with minute puberulent above, slightly sunken above and raised below.

Vein color: Adaxial midrib between RHS 187A and RHS 187B, lateral veins nearest RHS 138C; abaxial mid rib between RHS 145D and RHS 144D; abaxial lateral veins nearest RHS 144D near midrib and gradually darkening to nearest RHS 138B toward margin.

Petiole: Pubescent, slightly concaved above and convex below; about 7.0 mm long and 2.0 mm across at base.

Petiole color: Adaxial nearest RHS 187B with margins nearest RHS 139A; abaxial nearest RHS 138A at base and lightening to nearest RHS 144D.

Stems: Squared, puberulent, densely pubescent at nodes; about 4.0 mm across at base; about 34 per plant; naturally branched at upper nodes; average 1.8 cm between nodes greater distally; 15 to 18 nodes per stem; average length about 34 cm.

Stem color: Nearest RHS 144A with slight tinting of nearest RHS N186C in areas of strong direct light.

Flowers: Single labiate flowers arranged in mostly terminal verticillasters forming globular head about 7.0 cm across and 4.0 cm tall opening from the center and progressing outwardly and down; individual flowers persisting about 5 days in Michigan; numerous, about 200 flowers per terminal head, fewer per axillary head; beginning flowering in Michigan at least two weeks prior to typical *Monarda didyma* cultivars.

Flower fragrance: Moderately spicy.

Buds one to two days prior to opening: Narrowly oblanceolate, curved downward; about 2.5 cm long and 3 mm diameter and 4.0 mm tall; petals nearest RHS 72A above and below nearest RHS 72D with longitudinal stripes lighter than RHS 72D; younger bud color when petals just protruding beyond sepals nearest RHS 79B above with faded stripes with green tinting nearest RHS 145D.

Petals: Labiate; arched downward; base fused into tube; split in two in the distal 1.2 cm with upper lip fused into a hood about 3.0 cm long and 2.5 mm diameter, apex curved backward in distal 3.0 mm and fringed to densely pubescent; lower lip about 3.2 cm long comprising three lobes including two side lobes about 0.5 mm long with rounded apex and center lobe about 4.0 mm long split in the distal 1.0 mm; both petals glandular and pubescent on outer surfaces with fine hairs the same color as petals; both petals glabrous on inner surfaces; self-cleaning.

Petal color: Distal color of upper petal on both surfaces between RHS N78A and RHS 77A, inner surface near apex has two stripes 0.5 mm wide and 2.5 mm long nearest RHS 71A; with basal tube about 5.0 mm long near white, lighter than RHS 155D or RHS N155D; lower petal adaxial surface margins nearest RHS 72B with two lighter longitudinal strips nearest RHS 75D containing numerous irregular spots of nearest RHS 72A about 0.5 mm diameter in linear pattern longitudinal strips of nearest RHS 76C; and two other longitudinal strips of similar spots running almost on the petal margin; lower petal abaxial surface between RHS N80B and RHS N80C with darker margin of nearest RHS N81B, and near the longitudinal center two longitudinal strips of nearest RHS 76C with dark spotting showing through from adaxial petal surface.

Filaments: Two, curved downward; about 1.5 cm long by 0.5 mm diameter fused to petal about 1.5 cm from base; color at base nearest RHS 77C and darkening distally to nearest RHS 77A.

Anther: Oblong elliptic, dorsifixed, longitudinal; 2.2 mm by 1.0 mm; color nearest RHS N77A with longitudinal dehiscence line nearest RHS 187A.

Pollen: Abundant, elliptic to globose, less than 0.1 mm; color nearest RHS 12C.

Pistil: One per flower; protruding about 9.0 mm beyond upper petal when mature.

Style: About 3.8 cm long and less than 0.5 mm diameter; color nearest RHS 77A distally and lightening to near white, lighter than RHS 155D.

Stigma: Split in two in the distal 2.0 mm, 0.25 mm in diameter; color nearest RHS 77B.

Ovary: 1.0 mm by 0.75 mm; color between RHS 158A and RHS 150D.

Sepals: Five, apiculate apex, base fused forming corolla about 11.0 mm long and 2.5 mm diameter, fused in basal 9.0 mm to form a tube; glandular and with minute hairs on outer surface and especially at fusion opening; persistent.

Sepal color: Variable depending on light exposure; apex between RHS N187A and RHS N186A both adaxial and abaxial; distal two thirds of outer corolla surface between RHS N186B and RHS N187B with darker veins of RHS N187A, other sepals nearest RHS 187D with veins of RHS 187C; proximal half of outer corolla surface becoming lighter than RHS 145C without vein stripes; inner surfaces of tube nearest RHS 138B with veins of RHS 138A.

Foliar bracts: Usually two rows of six each in number; below verticillasters; lanceolate upper row and ovate to deltoid lower row; apex narrowly acute; base sessile, truncate; lower row of bracts about 3.2 cm long and 1.6 cm wide at base; upper row of bracts, about 1.8 cm long and 6.0 mm wide.

Foliar bract color: Variable depending on light exposure; adaxial surface nearest RHS 187C with green undertones of nearest RHS 137A other bracts nearest RHS 187D without green undertone; abaxial surface between RHS 137B and RHS 136B with tinting of RHS N187 A and RHS 187B; adaxial center vein color nearest RHS 60C and abaxial center vein color nearest RHS N187B with undertones of nearest RHS 137A; secondary adaxial and abaxial veins same color as surrounding tissue.

Peduncle: Pubescent, stiff, strong, erect, squared in cross-section to about 0.4 cm across and average 32 cm long; about 34 per plant; naturally branched at nodes; average 1.8 cm between nodes; 15 to 18 nodes per stem.

Peduncle color: Between RHS 146B and RHS 146C with tinting of nearest RHS 187B in regions of higher light exposure.

Pedicel: About 1.0 mm long and 0.5 mm diameter; color nearest RHS 145B.

Fruit: Single nutlet, elliptical, about 1.3 mm long and 0.7 mm wide; color nearest RHS 200C.

Hardiness: The new plant grows best with plenty of moisture and adequate drainage; hardy to at least from USDA zone 4 through 8.

Disease and pest resistance: Demonstrated greater than average powdery mildew tolerance in side by side comparison with other *Monarda.*

I claim:

1. A new and distinct cultivar of ornamental Bee balm plant, *Monarda* 'Leading Lady Plum', as herein described and illustrated, with compact habit, dark green foliage, earlier flowering with numerous magenta-purple flowers with darker reddish-purple spotting and tolerant to powdery mildew especially suitable as a potted plant, for the garden, patio, and for cut flower arrangements.

* * * * *